United States Patent [19]

Hunter et al.

[11] 3,975,374

[45] Aug. 17, 1976

[54] PROCESS FOR PREPARING 2-THIOURACIL NUCLEOSIDES

[75] Inventors: James H. Hunter; Harvey I. Skulnick, both of Kalamazoo, Mich.

[73] Assignee: The Upjohn Company, Kalamazoo, Mich.

[22] Filed: Jan. 7, 1974

[21] Appl. No.: 431,253

Related U.S. Application Data

[63] Continuation of Ser. No. 100,423, Dec. 21, 1970, abandoned.

[52] U.S. Cl. .................................. 536/23; 424/180
[51] Int. Cl.[2] ........................................ C07H 17/02
[58] Field of Search ........................... 260/211.5 R

[56] References Cited
UNITED STATES PATENTS 3,463,850  8/1969  Shen et al. ............... 260/211.5 R
3,708,469  1/1963  Vorbruggen et al. ...... 260/211.5 R

*Primary Examiner*—Johnnie R. Brown
*Attorney, Agent, or Firm*—John J. Killinger; Roman Saliwanchik

[57] ABSTRACT

Some new 1-(2- or 3-deoxy-β-D-pentofuranosyl)-2-thiouracils and 1-β-D-pentofuranosyl-2-thio-6-azauracils have been prepared. Further, it has been found that the known nucleoside compound, 1-β-D-ribofuranosyl-2-thiouracil is active against Herpes virus and against L-1210 leukemia in mice. An improved method of preparing corresponding 2-O-methyluracil and 2-O-methyl-6-azauracil intermediates is described. The method preserves the β-configuration of the starting nucleoside.

4 Claims, No Drawings

PROCESS FOR PREPARING 2-THIOURACIL NUCLEOSIDES

CROSS REFERENCE TO RELATED APPLICATIONS

This application is a continuation of application Ser. No. 100,423, filed Dec. 21, 1970, now abandoned.

SUMMARY OF THE INVENTION

This invention pertains to new organic chemical compounds, to a process for preparing them, to a new chemotherapeutic method, and to chemotherapeutic formulations. The invention is more particularly directed to new 1-(2- or 3-deoxy-β-D-pentofuranosyl)-2-thiouracils and 1-β-D-pentofuranosyl-2-thio-6-azauracils, a method of preparing the same which comprises treating a corresponding 2-O-methyluracil nucleoside or 2-O-methyl-6-azauracil nucleoside with hydrogen sulfide, a chemotherapeutic method against viruses and L1210 cells employing 1-β-D-pentofuranosyl-2-thiouracils and 1-β-D-pentofuranosyl-2-thio-6-azauracils, and formulations comprising the compounds for effecting the new method.

The new 1-(2- or 3-deoxy-β-D-pentofuranosyl)-2-thiouracils and 1-β-D-pentofuranosyl-2-thio-6-azauracils of this invention have the following general structural formula:

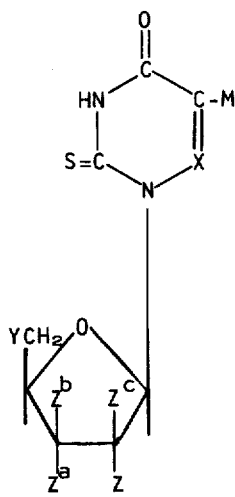

I wherein M is hydrogen, lower-alkyl of from 1 to 4 carbon atoms, inclusive; hydroxylower-alkyl of from 1 to 3 carbon atoms, inclusive, lower-alkoxy methyl of from 2 to 5 carbon atoms, inclusive, and lower-alkanoic acid esters of the hydroxy lower-alkyl having a total of from 3 to 6 carbon atoms, inclusive; X is =CH— or =N—; Y is hydroxyl, lower-alkanoyl of from 1 to 4 carbon atoms, inclusive, and aroyl of from 7 to 8 carbon atoms, inclusive; and Z, $Z^a$, $Z^b$, $Z^c$ are independently hydrogen, hydroxyl, lower-alkanoyl of from 1 to 4 carbon atoms, inclusive, and aroyl of from 7 to 8 carbon atoms, inclusive; providing that at least one but not more than two are hydroxyl, lower-alkanoyl, or aroyl at the same time, and further providing that $Z^b$ and $Z^c$, $Z^a$ and $Z^c$, Z and $Z^a$, and Z and $Z^b$ may not both be hydroxyl or lower-alkanoyl when X is =CH—.

The compounds effective in the chemotherapeutic method of this invention include the new compounds of the foregoing Formula I and 1-β-D-ribofuranosyl 2-thiouracil compounds of Formula I wherein $Z^a$ and Z are hydroxyl, lower-alkanoyl, or aroyl.

DETAILED DESCRIPTION

In the foregoing Formula I, the substituent M is contemplated as representing methyl, ethyl, propyl, butyl and isomeric forms thereof. M further represents, for example, hydroxymethyl, 2-hydroxyethyl, 3-hydroxypropyl, 1-hydroxyethyl, and 2-hydroxypropyl. Still further, M represents, for example, methoxymethyl, ethoxymethyl, propoxymethyl, isopropoxymethyl, and butoxymethyl. And finally, M represents, for example, acetoxymethyl, propionoxymethyl, 2-butyroxyethyl, and the like.

The substituents Z, $Z^a$, $Z^b$, $Z^c$, and Y when lower-alkanoyl represent, for example, acetyl (preferred), propionyl, butyryl, and isomeric forms thereof. These substituents when aroyl represent, for example, benzoyl, toluoyl, and anisoyl.

The β-D-pentofuranosyl sugars contemplated for X being =N— include, for example, ribose, arabinose, xylose, and lyxose including the deoxy forms thereof.

The 1-β-D-pentofuranosyl-2-thiouracils and 1-β-D-pentofuranosyl-2-thio-6-azauracils of this invention are prepared by an improved direct synthesis with hydrogen sulfide. In a preferred form of the process a solution of a 1-β-D-pentofuranosyl-2-O-methyluracil or 1-β-D-pentofuranosyl-2-O-methyl-6-azauracil is treated with hydrogen sulfide gas at a temperature in the range of 15° C. to 30° C. in the presence of a basic catalyst until the 2-O-methyl group is replaced by a sulfur atom. The desired product is readily recovered in relatively pure form and in generally good yields by conventional methods of solvent evaporation and chromatographic purification.

The starting 1-β-D-pentofuranosyl-2-O-methyluracils and -2-O-methyl-6-azauracils are in general known compounds preparable according to methods described by Brown, Todd, and Varadarajan, J. Chem. Soc. p. 868 (1957).

An improved procedure according to this invention involves reacting a 2,5'-anhydro-1-β-D-pentofuranosyluracil or -6-azauracil with methanol in the presence of an alkali metal alkoxide. The prior art has used ammonia and triethylamine as the basic catalyst but in some instances the reactions are prohibitively slow.

One could use an alcohol other than methanol, e.g., ethanol and propyl alcohol; and effective alkali metal alkoxides include, for example, sodium methoxide (preferred), sodium ethoxide, sodium propoxide, and potassium methoxide. This reaction progresses cleanly at temperatures in the range of 25° C., but slightly higher temperatures can be used, e.g., up to about 40° C.

The desired 1-β-D-pentofuranosyl-2-O-methyluracil or 1-β-D-pentofuranosyl-2-O-methyl-6-azauracil is recovered by neutralizing the reaction mixture with portions of acid, e.g., a lower alkanoic acid, illustratively acetic acid (preferred) or propionic acid, removing the solvent medium, and purifying by conventional methods, e.g., chromatography, solvent crystallization, and the like.

The 2,5'-anhydro-1-β-D-pentofuranosyl uracil and -6-azauracil starting compounds are known or can be prepared by known methods as described in the literature and the illustrative preparations herein.

The activity of the compounds of this invention against viruses and L1210 cells has been observed in both in vitro and in vivo tests. Preliminary tests against tissue culture propagated L-1210 leukemia cells showed that 1-β-D-ribofuranosyl-2-thio-6-azauracil is active at very low concentrations. Illustratively, an $ID_{50}$ dosage is 0.06 μg./ml., and an $ID_{90}$ dosage is 0.23 μg./ml.

A confirming test in mice wherein the test mice received $1 \times 10^6$ ascitic tumor cells (L 1210) and the compound 1-β-D-ribofuranosyl-2-thio-6-azauracil was administered at a daily dosage of 200 mg./kg., intraperitoneally, for 8 days, showed that the treated mice had an increased life span calculated to be 47% longer than the post-infection life span of untreated (control) mice.

From the foregoing preliminary observations the daily dosage for mammals is projected to be from about 10 mg. to about 400 mg. per kilogram of body weight. It being understood, of course, that the dosage will vary depending upon the kind of animal, e.g., dog, cat, cow, horse, mouse, rat, the age of the animal, the severity of the condition, and the vigor of the animal. Single daily, multiple daily, or intermittent daily schedules can be followed.

Similar outstanding efficacy has been found for the compounds of this invention when they are tested against viruses. In various tests, that have been conducted, the compounds 1-β-D-ribofuranosyl-2-thio-6-azauracil, 1-β-D-ribofuranosyl-2-thiouracil, 1-(2-deoxy-β-D-erythropentofuranosyl)-2-thiothymine, 1-(3,5-di-O-acetyl-2-deoxy-β-D-erythropentofuranosyl)-2-thiothymine, 1-(2-deoxy-β-D-erythropentofuranosyl)-2-thiouracil, 1-(3,5-di-O-acetyl-2-deoxy-β-D-erythropentofuranosyl)-2-thiouracil, and 1-(2-deoxy-β-D-threopentofuranosyl)-2-thiothymine have been rated 3 to 4+ (top) for their activity against Herpes virus. The compounds are also active against Coe virus and HA-1 virus.

Some preferred compounds in accordance with the invention are the anti-viral 1-(2- or 3-deoxy-β-D-erythropentofuranosyl)-2-thiouracils, particularly 1-(3,5-di-O-acetyl-2-deoxy-β-D-erythropentofuranosyl)-2-thiothymine, and 1-(3,5-di-O-acetyl-2-deoxy-β-D-erythropentofuranosyl)-2-thiouracil.

Some other preferred compounds in accordance with the invention are the 1-β-D-pentofuranosyl-2-thio-6-azauracils, particularly 1-β-D-ribofuranosyl-2-thio-6-azauracils, more particularly 1-β-D-ribofuranosyl)-2-thio-6-azauracil and its 2',3',5'-triacetate.

The valuable anti-viral activity of the 1-β-D-pentofuranosyl-2-thiouracils and -2-thio-6-azauracils of this invention is utilized contacting the compounds with the virus to be controlled. The desired contact is accomplished by infusing them by well-known methods into the milieu containing the virus. Hence, for example, a respiratory syncytial virus infection of chimpanzees can be controlled by applying 1-(3,5-di-O-acetyl-2-deoxy-β-D-erythropentofuranosyl)-2-thiothymine or 1-(2-deoxy-β-D-threopentofuranosyl)-2-thiothymine to the mucus membranes of the nose and throat at about a 1% concentration. The compound thus applied to an infected or proximate tissue becomes dispersed throughout the tissue fluids and thus contacts the virus at the site of infection. The desired contact can also be accomplished systemically by formulating the compounds in compositions for oral or parenteral administration.

For oral administration the active compounds can be formulated with a pharmaceutical carrier to give solid or fluid unit dosage forms.

Suitable solid forms include tablets, pills, capsules, granules, powders, suppositories, and the like. Advantageously, the pharmaceutical carrier for such solid forms include corn starch, lactose, dicalcium phosphate, terra alba (calcium sulfate), talc, stearic acid, magnesium stearate, and gums. Suitable fluid forms include solutions, suspensions, syrups, and emulsions. Advantageously, the pharmaceutical carrier for such fluid forms comprise water, oils, and water-oil emulsions. If desired, suitable dispersing or suspending agents can be included, for example, tragacanth, acacia, alginates, dextran, sodium carboxymethyl-cellulose, methylcellulose, polyvinyl pyrrolidone, gelatin, and mixtures thereof. Suitable oils for solutions and water-oil emulsions include cottonseed oil, sesame oil, coconut oil, and peanut oil.

For parenteral administration, 1-β-D-pentofuranosyl-2-thiouracils and -2-thio-6-azauracils can be formulated in dilute aqueous solutions, aqueous suspension, and oil dispersions for intramuscular injection, intravenous drip, vascular perfusion, or like routes. Advantageously, a solubilizer, for example, N,N-dimethylacetamide (preferred), N,N-dimethylformamide, ethanol, and the like can be utilized. If desired, other aqueous media such as water for injection, normal saline solution, Ringer's solution, blood plasma, and whole blood can be used.

Formulations of the compounds of this invention for topical applications include powders (preferred), ointments, creams, pastes, jellies, and the like. Such compositions of the essential active ingredient can include emulsifying agents, solvents, antioxidants, preservatives, buffers, and bodying materials.

The following examples are illustrative of the process and products of the present invention. They are not to be construed as limiting.

EXAMPLE 1

Preparation of
1-β-D-Ribofuranosyl-2-Thio-6-Azauracil

Part A.
1-(2,3-O-Isopropylidene-β-D-ribofuranosyl)-6-azauracil

With all moisture excluded, a suspension consisting of 245 mg. (1.0 millimole) 2-β-D-ribofuranosyl-as-triazine-(2H,4H)-dione, 490 mg. (3.8 millimoles) anhydrous cupric sulfate, and 10 ml. acetone acidified with 0.01 ml. concentrated sulfuric acid was stirred continuously for about 24 hrs. The suspension was then filtered and the filtrate was adjusted to neutral pH by dropwise additions of 1.0 N aqueous sodium hydroxide. The neutralized filtrate was then evaporated to dryness under reduced pressure. The dry residue was dispersed in a mixture of chloroform and water and the organic phase was separated from the aqueous phase. The aqueous phase was extracted several times with chloroform, and the extracts were combined with the separated chloroform layer. After drying the chloroform solution, the chloroform was removed by evaporation under reduced pressure. There was thus obtained a white solid that upon crystallization from a mixture of acetone and methylcyclohexane yielded 62.5 mg. of 1-(2,3-O-isopropylidene-β-D-ribofuranosyl)-6-azauracil having a melting point at 141.5° to 143° C.

Ultraviolet Absorption: $\lambda_{max.}^{absolute\ ethanol}$ 261 mμ (ε 7,000).

Characteristic infrared absorption frequencies (cm.$^{-1}$) OH/NH, 3530; NH/=CH/OH, 3140, 3080, 2950; C=O/C=N, 1585$_w$; C—O/C—N/other, 12,75; 1205, 1165, 1135, 1115, 1070, 1055; Other, 870.

Analysis: Calc'd. for $C_{11}H_{15}N_3O_6$: C, 46.31; H, 5.30; N, 14.73. Found: C, 46.31; H, 5.52; N, 14.96.

Part B.
1-(5-O-Tosyl-2,3-O-isopropylidene-β-D-ribofuranosyl)-6-azauracil With all moisture excluded, a solution consisting of 2.58 g. (13.5 millimoles) of purified p-toluenesulfonyl chloride and 26 ml. pyridine was added dropwise to a stirred solution consisting of 4.39 g. (approximately 10 millimoles) 1-(2,3-O-isopropylidene-β-D-ribofuranosyl)-6-azauracil (prepared as in Part A, above) and 26 ml. pyridine that had been chilled to minus 10° C. During the addition, the temperature was maintained in the range of 0° C. to −10° C. The flask containing the p-toluenesulfonyl chloride was rinsed with an additional 4 ml. pyridine, and the rinse was added to the reaction mixture. The mixture was set aside for about 16 hrs. at about 3° C. The reaction mixture became dark, and crushed ice was added. It was then set aside at about 3° C. for several more days. After removing the pyridine and water by evaporation under reduced pressure, the residue was azeotroped with absolute ethanol under reduced pressure. The non-volatile residue remaining was dispersed in a mixture of chloroform and water (75 parts: 15 parts). After separating the chloroform layer from the aqueous layer in a separatory funnel, the chloroform layer was washed with clean water. The washed chloroform solution (which was dark) was then dried over anhydrous sodium sulfate, and the chloroform was removed by evaporation under reduced pressure. The residue thus obtained was dissolved in hot absolute ethanol and decolorizing charcoal was added to the solution. The charcoal was removed by filtering, and the charcoal on the filter was washed with absolute ethanol. After a second decolorizing with charcoal as described, the alcohol was removed by evaporation under reduced pressure. The residue thus obtained (a yellow solid) was azeotroped under reduced pressure two times using 95% aqueous ethanol. The residue thus obtained was held under vacuum in order to remove traces of pyridine. This pyridine-free residue was dissolved in acetone and decolorizing charcoal was added. The charcoal was removed by filtering and the charcoal on the filter was washed with acetone. The acetone filtrate was then concentrated to a volume of about 75 ml. and the concentrate was diluted with 50 ml. technical hexane (Skellysolve B, a mixture of isomeric hexanes having a boiling point of 60° to 71° C.). The diluted solution was seeded with crystals, set aside at about 25° C. for 16 hrs., and then refrigerated at 3° C. for several hrs. The crystals that formed were collected on a filter, washed well with diethyl ether and dried under high vacuum at 25° C. There was thus obtained 2.12 g. of 1-(5-O-tosyl-2,3-O-isopropylidene-β-D-ribofuranosyl)-6-azauracil having a melting point at 156° to 158° C.

Part C.
2,5'-Anhydro-1-(2,3-O-isopropylidene-β-D-ribofuranosyl)-6-azauracil A mixture consisting of 300 mg. (0.705 millimole) 1-(5-O-tosyl-2,3-O-isopropylidene-β-D-ribofuranosyl)-6-azauracil (Part B, above), 10 ml. dimethylformamide and 325 mg. sodium bicarbonate was heated and stirred (moisture being excluded) at 150° C. in an atmosphere of nitrogen for 10 min. After cooling the reaction mixture to 25° C., filtering, and thoroughly washing the filter with dimethylformamide, the combined filtrate and washings was evaporated to dryness under reduced pressure. The residue thus obtained was azeotroped two times with absolute ethanol under reduced pressure and a yellow solid was obtained. The solid was dissolved in 95% aqueous ethanol, and 2.5 g. silica gel was added. The slurry thus obtained was taken to dryness by evaporating the aqueous ethanol under reduced pressure. The dried silica gel was placed on a column of silica gel (28 g.) moistened with "Solvent A" (A mixture of ethyl acetate, technical hexane, and methanol in proportions 6:3:1, respectively) and the desired product was eluted with additional "Solvent A". After removing the "Solvent A" by evaporation under reduced pressure the 79.1 mg. of residue was crystallized from a mixture of acetone and the technical hexane. There was thus obtained 63.1 mg. of 2,5'-anhydro-1-(2,3-O-isopropylidene-β-D-ribofuranosyl)-6-azauracil that had no definite melting point.

Ultraviolet Absorption: $\lambda_{max.}^{95\%\ EtOH}$ 236; 260 sl.sh. mμ (ε 12,100; 5,950).

Characteristic infrared absorption frequencies (cm.$^{-1}$) C=O/C=N, 1675, 1595; C—O/C—N/other, 1285, 1260, 1205, 1095, 1065; Other, 910, 855.

Analysis: Calc'd. for $C_{11}H_{13}N_2O_5$: C, 49.43; H, 4.90; N, 15.73. Found: C, 49.33; H, 5.16; N, 15.53.

Part D.
1-(2,3-O-Isopropylidene-β-D-ribofuranosyl)-2-thio-6-azauracil

A solution consisting of 68.4 mg. (0.256 millimole) 2,5'-anhydro-1-(2,3-O-isopropylidene-β-D-ribofuranosyl)-6-azauracil (prepared in Part C, above), 2 ml. dimethylformamide, and three drops triethylamine was treated with hydrogen sulfide gas by slowly bubbling the gas through the reaction mixture during one-half hr. The solution was then taken to dryness by evaporating the solvent under reduced pressure. The residue thus obtained was azeotroped two times with absolute ethanol under reduced pressure, and 1-(2,3-O-isopropylidene-β-D-ribofuranosyl)-2-thio-6-azauracil as an amorphous solid was obtained.

Part E. 1-β-D-Ribofuranosyl-2-thio-6-azauracil

The crude 1-(2,3-O-isopropylidene-β-D-ribofuranosyl)-2-thio-6-azauracil [prepared as in Part D, above, from 84.1 mg. (0.315 millimole) of 2,5'-anhydro-1-(2,3-O-isopropylidene-β-D-ribofuranosyl)-6-azauracil prepared as in Part C, above] was dissolved in 4 ml. of a mixture of 9 parts trifluoroacetic acid and 1 part water and the solution was set aside at 25° C. for 25 minutes. After removing the volatile components by evaporation under reduced pressure, the residue thus obtained was azeotroped two times with 95% aqueous ethanol under reduced pressure. The azeotroped residue was again treated with the 9:1 mixture of trifluoroacetic acid for 30 min. and this reaction mixture was worked up as described above. The azeotroped residue was dissolved in 1 ml. ethanol and the ethanolic solution was put on a column of silica gel (20 g.) that had been moistened with a 1:1 mixture of "Solvents A and B" (Solvent B is mixture of ethyl acetate, technical hexane, and methanol in proportions 8:12:1, respectively). The desired product was eluted from the column with the same 1:1 solvent mixture, 1 ml. fractions being collected. Fractions 46 through 50 were combined, and the solvents evaporated under reduced pressure to give 1-β-D-ribofuranosyl-2-thio-6-azauracil.

Ultraviolet Absorption: $\lambda_{max}^{95\%\ EtOH}$ 219; 272.5 mμ

EXAMPLE 2

Preparation of 1-β-D-Ribofuranosyl-2-Thiouracil

Part A.
1-(2,3-O-isopropylidene-β-D-ribofuranosyl)-2-thiouracil

A solution consisting of 744 mg. (2.5 millimoles) 1-(2,3-O-isopropylidene-β-D-ribofuranosyl)-2-O-methyluracil, [prepared according to the method of Brown, Todd, and Varadarajan, J. Chem. Soc. p. 868 (1957)], 9 ml. dimethylformamide, and 0.45 ml. redistilled triethylamine was treated with hydrogen sulfide by gently bubbling a stream of the gas through the solution for 20 hrs. A green solution was obtained. The solvent and volatile components were removed by evaporation under reduced pressure, and the residue thus-obtained was azeotroped three times with benzene under reduced pressure. There was thus obtained 850 mg. of an amorphous yellow foam. The foam was dispersed in 6 ml. of warm "Solvent A" and the mixture was set aside for several days at 25° C. Crystals formed, which were collected on a filter, washed with their mother liquor filtrate and then with cold "Solvent A". The combined filtrate and washings was taken to dryness by evaporating the solvent under reduced pressure. The residue thus obtained was amorphous. It was dissolved in chloroform, and silica gel was added to the solution to a slurry. The chloroform was then removed by evaporation and the dry silica gel adsorbate was added to a column of silica gel that had been wetted with "Solvent A". The column was developed with "Solvent A", and 5 ml. fractions were collected. Fractions 30 through 39 were combined and taken to dryness by evaporating the solvent under reduced pressure. There was thus obtained 1-(2,3-O-isopropylidene-β-D-ribofuranosyl)-2-thiouracil in an amorphous state that according to thin layer chromatographic comparison was essentially identical with 1-(2,3-isopropylidene-β-D--ribofuranosyl)-2-thiouracil prepared according to the method of Brown et al. J. Chem. Soc. p. 868 (1957).

The foregoing preparation was repeated collecting the early fractions with the more mobile component. Crystallization from ethyl acetate gave 1-(2,3-O-isopropylidene-β-D-ribofuranosyl)-2-thiouracil having a melting point at 194.5° to 198° C.

Optical Rotations: $[\alpha]_D^{23°}$ −41° (C, 0.7276 in 95% ethanol).

Ultraviolet Absorption: $\lambda_{max}^{75\%\ EtOH}$ 219; 274 mμ (ε 17,300; 14,750)

Characteristic infrared absorption frequencies (cm.$^{-1}$) NH/OH, 3500, 3200, 3120, 3080; C=O, 1690; C=C/C=N, 1640, 1620, 1490; C=S/C—O/C—N/other, 1275, 1255, 1220, 1550, 1110, 1080, 1070; Other, 890, 835.

Analysis: Calc'd. for $C_{12}H_{16}N_2O_5S$: C, 47.98; H, 5.37; N, 9.33; S, 10.68. Found: C, 47.92; H, 5.43; N, 9.43; S, 10.70.

Part B. 1-β-D-Ribofuranosyl-2-thiouracil

A sample of the amorphous 1-(2,3-O-isopropylidene-β-D-ribofuranosyl)-2-thiouracil from fractions 30 through 39 (Part A, above) and 1 ml. of 1N hydrochloride acid was heated at the reflux temperature for 4 min. The resulting aqueous acid solution was evaporated to dryness under reduced pressure, and the residue was dissolved in water followed by removal of the water again by evaporation under reduced pressure. After two recrystallizations from water there was obtained 1-β-D-ribofuranosyl-2-thiouracil having a melting point at 206° to 209° C.

Ultraviolet Absorption: $\lambda_{max}^{0.1\ N\ NaOH}$ 239; 270.

EXAMPLE 3

Preparation of 1-β-D-Ribofuranosyl-2-Thiothymine

Part A.
1-(2,3-O-Isopropylidene-β-D-ribofuranosyl)thymine

With all moisture excluded, a reaction mixture suspension consisting of 5.95 g. (23.0 millimoles) 1-β-D-ribofuranosylthymine, 11.25 g. anhydrous cupric sulfate, 230 ml. acetone, and 0.23 ml. concentrated sulfuric acid was stirred continuously for 40 hrs. at 25° C. The reaction suspension was then filtered through a bed of "Celite" (A diatomaceous silic product used as a filter aid) and the filter cake was washed thoroughly with acetone. After combining the filtrate and washings, 5.5 g. calcium hydroxide was added. This mixture was stirred for 5 hrs. at 25° C. while all moisture was excluded. The mixture was then filtered through a bed of "Celite" and the filter cake was again thoroughly washed with acetone. The combined filtrate and acetone washings was then taken to dryness by evaporating the acetone under reduced pressure. The white foam thus obtained was azeotroped two times with ethyl acetate under reduced pressure. The solids that remained were dissolved in hot methanol, followed by removal of the methanol by evaporation under reduced pressure. The white, non-crystalline residue thus obtained was held under high vacuum at 50° C. (bath temperature) for 1¾ hrs. There was thus obtained 7.06 g. of 1-(2,3-O-isopropylidene-β-D-ribofuranosyl)thymine.

Part B.
1-(5-O-Tosyl-2,3,-O-isopropylidene-β-D-ribofuranosyl)thymine

After dissolving 6.56 g. (22.0 millimoles) 1-(2,3-O-isopropylidene-β-D-ribofuranosyl)thymine (Part A, above) in pyridine, there was added to the solution 4.61 g. (24.2 millimoles) of freshly crystallized p-toluenesulfonyl chloride (the traces of which were washed into the reaction mixture with a small amount of pyridine) (the total amount of pyridine in the reaction mixture was 37 ml.). The reaction vessel was closed securely and set aside in semi-darkness for 24 hrs. After adding 3 ml. water to the reaction mixture it was set aside for another hour. The reaction mixture was then poured with stirring into 140 ml. water. A gummy substance separated and the aqueous supernatant was decanted. The supernatant was extracted five times with 30 ml. portions chloroform. The chloroform extracts were combined, and the gummy substance was dissolved in the extracts. This chloroform solution was washed, successively, three times with water, three times with 10 per cent aqueous potassium bisulfite two times with cold saturated sodium bicarbonate, and two times with ice-water. The washed chloroform solution was treated with decolorizing charcoal for several hours with intermittent swirling. It was then filtered through "Celite". The charcoal on the filter was washed with chloroform, and the combined filtrate and washings were dried over anhydrous sodium sulfate. After removing the chloroform by evaporation under reduced pressure the foamy residue was dissolved in hot 95% aqueous ethanol. The aqueous ethanol was removed by evaporation under high vacuum at a bath temperature of 50° C. The residue thus obtained was azeotroped two more times with 95% aqueous ethanol under high vacuum and the amorphous residue thus obtained was held under high vacuum for 2½ hrs. at 50° C. There was thus obtained 8.42 g. of 1(5-O-tosyl-2,3-O-isopropylidene-$\beta$-D-ribofuranosyl)thymine.

Part C.
2,5'-Anhydro-1-(2,3-O-isopropylidene-$\beta$-D-ribofuranosyl)thymine.

A solution consisting of 1.0 g. (2.21 millimoles) of 1-(5-O-tosyl-2,3-O-isopropylidene-$\beta$-D-ribofuranosyl)thymine (Part B, above), 12 ml. dimethylformamide, and 1.0 g. sodium bicarbonate was heated with stirring and nitrogen atmosphere at an oil-bath temperature of 150° to 160° C. for 45 mins. The reaction mixture darkened. It was filtered and the filter was washed with dimethylformamide. The combined filtrate and washings were taken to dryness by evaporating the dimethylformamide under reduced pressure. The residue thus obtained was azeotroped three times with absolute ethanol under reduced pressure. The resulting solid was dissolved in warm 90% aqueous ethanol and 2.5 g. silica gel was added. The silica gel slurry was taken to dryness by evaporating the 90% aqueous ethanol under reduced pressure. The dry silica gel containing the compound, was added to a column of silica gel that had been wetted with "Solvent A". The compound was eluted with "Solvent A". Removal of the "Solvent A" from the eluate under reduced pressure gave a white solid, which when crystallized from a mixture of absolute ethanol and technical hexane afforded 356 mg. of 2,5'-anhydro-1-(2,3-O-isopropylidene-$\beta$-D-ribofuranosyl)thymine having an indefinite melting point.

Ultraviolet Absorption: $\lambda_{max.}^{95\% \ EtOH}$ 246 m$\mu$ ($\epsilon$ 12.400).

Characteristic infrared absorption frequencies (cm.$^{-1}$) C=O/C=N/C=C, 1650, 1545; C—O/C—N/other, 1295, 1285, 1210, 1155, 1145, 1095, 1065, 1055; Other, 860, 790.

Analysis: Calc'd. for $C_{13}H_{16}N_2O_5$: C, 55.71; H, 5.75; N, 10.00. Found: C, 55.89; H, 6.00; N, 10.09.

Part D.
1-(2,3-O-Isopropylidene-$\beta$-D-ribofuranosyl)-2-O-methylthymine

A warmed solution consisting of 280 mg. (1.0 millimole) 2,5'-anhydro-1-(2,3-O-isopropylidene-$\beta$-D-ribofuranosyl)-thymine (Part C, above) and 2 ml. dimethylformamide was cooled under tap water (about 25° C.), and 20 ml. absolute methanol and 21 mg. sodium methoxide were added. The reaction vessel was closed securely and set aside at 25°C. for 17 hrs. Afterwards, the reaction solution was neutralized, dropwise, with glacial acetic acid, and the liquid components were removed by evaporation under reduced pressure. The white solid thus obtained was triturated thoroughly with acetone, the acetone solution was filtered, and the filter was washed with acetone. The combined filtrate and acetone washings (about 15 ml.) was diluted with technical hexane, to cloudiness which dilution caused immediate crystallization. After setting the crystallizing solution aside at 25° C. for 16 hrs., the crystals were collected on a filter, washed with a mixture of acetone and technical hexane, and dried. There was thus obtained 222.7 mg. of 1-(2,3-O-isopropylidene-$\beta$-D-ribofuranosyl)-2-O-methylthymine having a melting point at 164.5° to 168° C.

Ultraviolet Absorption: $\lambda_{max.}^{95\% \ EtOH}$ 231 sh.; 252 m$\mu$ ($\epsilon$ 9,000; 11,700).

Characteristic infrared absorption frequencies (cm.$^{-1}$) OH, 3250; C=O/C=N/C=C, 1655, 1605, 1570$_w$; 1520; C—O/C—N/other, 1290, 1270, 1240, 1210, 1155, 1125, 1110, 1095, 1060, 1025, 1010; Other, 870, 785.

Analysis: Calc'd. for $C_{14}H_{20}N_2O_6$: C, 53.84; H, 6.45; N, 8.97. Found: C, 53.82; H, 6.22; N, 8.87.

Part E.
1-(2,3-O-Isopropylidene-$\beta$-D-ribofuranosyl)-2-thiothymine

A solution consisting of 158 mg. (0.505 millimole) of 1-(2,3-O-isopropylidene-$\beta$-D-ribofuranosyl)-2-O-methylthymine (Part D, above), 5 ml. dimethylformamide, and 0.4 ml. triethylamine was treated with hydrogen sulfide by slowly bubbling a stream of the gas through the reaction mixture. The treatment was continued for 18 hrs. at 25° C. Afterwards, any excess hydrogen sulfide was removed by purging with a stream of nitrogen gas. The hydrogen sulfide-free reaction mixture thus obtained was poured through a filter into a roundbottom flask and the volatile components were removed by evaporation under reduced pressure. The residue thus obtained was azeotroped three times with absolute ethanol removed by evaporation under reduced pressure. The azeotroped solid was slurried with silica gel and the slurry was added to a column of silica gel wetted with "Solvent A". The column was developed with "Solvent A", and 1 ml. fractions were collected. Fractions 41 through 48 were combined, and the "Solvent A" was removed by evaporation under reduced pressure. The resulting solid was recrystallized from a mixture of acetone and technical hexane to give 51.4 mg. of 1-(2,3-O-isopropylidene-$\beta$-D-robufuranosyl)-2-thiothymine having a melting point at 213° to 215° C.

Ultraviolet Absorption: $\lambda_{max.}^{95\% \ EtOH}$ 222; 279.5 m$\mu$ ($\epsilon$ 16,150, 17,550)

Characteristic infrared absorption frequencies (cm$^{-1}$) OH/NH, 3530, 3330, 3220$_{sh}$; C=O/C=C, 1670, 1605, 1490; C—O/C—N/other, 1295, 1275, 1270, 1230, 1220, 1160, 1105, 1090; Other, 850.

Analysis: Calc'd. for $C_{13}H_{18}N_2O_5S$: C, 49.67; H, 5.77; N, 8.91; S, 10.20. Found: C, 49.30; H, 6.25; N, 8.55; S, 10.09.

Part F. 1-$\beta$-D-Ribofuranosyl-2-thiothymine

A solution consisting of 300 mg. (0.955 millimole) of 1-(2,3-O-isopropylidene-$\beta$-D-ribofuranosyl)-2-thiothymine (prepared as in Part E, above) and 4.5 ml. of 90% aqueous trifluoroacetic acid in a securely stoppered flask was allowed to react for 10 mins. at 25° C. The volatile components were then removed by evaporation under reduced pressure, and the residue thus obtained was azeotroped three times with absolute ethanol under reduced pressure. The solid residue thus obtained was transferred to a clean flask using methanol as a wash liquid and the methanol was removed by evaporation under reduced pressure. The solid thus obtained was triturated with absolute ethanol, and the ethanol was removed by evaporation under reduced pressure. There was thus obtained a crystalline solid that was held under high vacuum for several hrs. at 55°C. (bath temperature). The evacuated crystals melted at 198° to 201° C. Recrystallization from a mixture of absolute ethanol and technical hexane gave an analytical sample melting at 206° to 208.5° C.

Optical Rotation: $[\alpha]_D^{23°}$ +1 (C, 0.4772 in dimethylformamide).

Ultraviolet Absorption: $\lambda_{max.}^{95\% \; EtOH}$ 222; 277; 285$_{sh.}$ m$\mu$ ($\epsilon$ 20,000, 20,850; 19,900)

Charcteristic infrared absorption frequencies (cm$^{-1}$) NH/OH, 3460, 3420, 3350, 3260; C=O/C=C, 1685$_{sh.}$, 1665, 1490; C—N/C=S/C—O/other, 1265, 1235, 1165, 1130, 1100, 1080, 1055, 1040.

Analysis: Calc'd. for $C_{10}H_{14}N_2O_5S$: C, 43.78; H, 5.14; N, 10.22; S, 11.68. Found: C, 44.18; H, 5.90; N, 10.27; S, 11.42.

EXAMPLE 4

Preparation of 1-(2-Deoxy$\beta$-D-Erythropentofuranosyl)-2-Thiothymine and the 3,5-Di-O-Acetate Thereof

Part A.

1-(2-Deoxy-$\beta$-D-erythropentofuranosyl)-2-O-methylthymine

To a solution consisting of 410 ml. absolute methanol and 1.12 g. (5.0 millimoles) 2,5'-anhydro-1-(2-deoxy-$\beta$-D-erythropentofuranosyl)thymine [prepared according to the method described by Michelson and Todd, J. Chem. Soc., p. 816 (1953)] was added 4 ml. methanol that had been saturated with anhydrous ammonia at 0° to −5° C. The reaction flask was stoppered securely, set aside at 25° C., and the progress of the reaction was monitored by thin layer chromatography using "Solvent C" (A mixture of ethyl acetate, technical hexane, and methanol in proportions 5:2:3, respectively). After 120 hrs. when the reaction had proceeded only to the extent of 30%, an additional 7 ml. of saturated methanolic ammonia was added. After a further 2 weeks' reaction time, when the reaction appeared to be complete, the methanol and any residual ammonia were removed by evaporation under reduced pressure. The residue thus obtained was azeotroped two times with absolute ethanol under reduced pressure, and the white crystalline substance thus obtained was held under high vacuum for 2 hrs. A 100 mg. sample of the crystals was recrystallized from a mixture of absolute methanol and absolute ether to give 1-(2-deoxy-$\beta$-D-erythropentofuranosyl)-2-O-methylthymine having a melting point at 148.5° to 151° C.

Ultraviolet Absorption: $\lambda_{max.}^{95\% \; EtOH}$ 233$_{sh.}$; 252 m$\mu$ ($\epsilon$ 8,800; 10,550)

Characteristic infrared absorption frequencies (cm$^{-1}$) OH/=CH, 3420, 3380, 3160, 3080; C=O/C=C, 1650, 1610$_{sh.}$; 1600, 1570, 1515, 1485; C—O/C—N-/other, 1290, 1190, 1110, 1075, 1030, 1010, 1000; Other, 845, 785.

Analysis: Calc'd. for $C_{11}H_{16}N_2O_5$: C, 51.56; H, 6.29; N, 10.93. Found: C, 51.71; H, 6.15; N, 10.88.

Part B.

1-(2-Deoxy-$\beta$-D-erythropentofuranosyl)-2-thiothymine

While moisture was excluded, a suspension consisting of 190 mg. (0.742 millimole) of 1-(2-deoxy-$\beta$-D-erythropentofuranosyl)-2-O-methylthymine (Part A, above) and 6 ml. dimethylformamide was purged with a bubbling stream of dry nitrogen gas. Then, 0.37 ml. triethylamine was added and further purging with dry nitrogen was continued for 10 minutes. The nitrogen purging was stopped and a slowly bubbling stream of hydrogen sulfide gas was continued for 26 hrs. After this treatment, there was still a small amount of undissolved starting compound, but the reaction mixture was transferred to a clean roundbottom flast aided by a dimethylformamide rinse. The dimethylformamide was removed by evaporation under reduced pressure, and the residue thus obtained was azeotroped three times with anhydrous benzene, the benzene being removed under reduced pressure. The semisolid residue thus obtained was triturated thoroughly with acetone, and the acetone insoluble portion was removed by filtering. The acetone was removed from the filtrate by evaporation and 147.5 g. of a semi-crystalline substance was obtained. The substance was chromatographed of a column of silica gel (18.5 g.) using "Solvent C" for development. Fractions of 1.5 ml. were collected and the solvent in fractions 19 through 23 was allowed to evaporate. An essentially white crystalline residue was obtained, and these residues were taken up in methanol. After combining the fractions in methanol and removing the methanol by evaporation under reduced pressure, there was obtained 35.2 mg. of 1-(2-deoxy-$\beta$-D-erythropentofuranosyl)-2-thiothymine having a melting point at 173° to 175° C.

Ultraviolet Absorption: $\lambda_{max.}^{0.1 \; N \; HCl}$ 220; 278 m$\mu$ ($\epsilon$15,250; 17,000). $\lambda_{max.}^{0.1 \; N \; NaOH}$ 241; 265$_{sl.sh.}$m$\mu$ ($\epsilon$23,800; 14,950)

Characteristic infrared absorption frequencies (cm.$^{-1}$) NH/OH/=CH, 3140, 3090, 3060; C=O/C=C/C=N, 1695, 1680, 1635$_{w.sh.}$, 1500; C=S/C—N/C—O/other, 1310, 1280, 1230, 1185, 1145, 1105, 1070, 1060, 1010.

Analysis: Calc'd. for $C_{10}H_{14}N_2O_4S$: C, 46.50; H, 5.96; N, 10.85; S, 12.42. Found: C, 46.60; H, 5.80; N, 10.87; S, 12.48.

The foregoing preparation was repeated in scale about 2.6 × larger. A final recrystallization from a mixture of absolute ethanol and technical hexane yielded the compound having a melting point at 175° to 176° C.

Optical Rotation: $[\alpha]_D^{23°}$ +44° (C, 0.4322 in 0.1 N sodium hydroxide)

Ultraviolet Absorption: $\lambda_{max.}^{H_2O}$ 221; 277 m$\mu$ ($\epsilon$15,100; 16,850)

Characteristic infrared absorption frequencies (cm.$^{-1}$)

Same as those of the preparation above.

Mass Spectroscopy: M$^+$ 258; B +1, 142.

Analysis: Found: C, 46.39; H, 5.24; N, 11.12; S, 12.12.

Confirmation that the compound was in the $\beta$-anomeric configuration was established when it was rapidly cleaved by *Escherichia coli* phosphorylase.

Part C.
1-(3,5-Di-O-acetyl-2-deoxy-β-D-erythropentofuranosyl)-2-thiothymine A suspension consisting of 516 mg. (2.0 millimoles) of finely divided 1-(2-deoxy-β-D-erythopentofuranosyl-2-thiothymine, 4.0 ml. acetic anhydride, and 2 drops pyridine was heated, with moisture excluded, at a bath temperature of 76° to 80° C. for about 72 hrs. The reaction mixture was allowed to cool gradually and was then added to an excess of crushed ice and water in a beaker. The reaction vessel was rinsed with a small amount of pyridine, and the rinsings were added to the beaker of ice and water. Crystallization occurred spontaneously after stirring the mixture and scratching the sides and bottom of the beaker. The crystallization reaction product in the ice and water was left undisturbed for 1½ hrs., and it was then refrigerated for 3 hrs. at 3° C. The crystals were then collected on a filter, and the filter cake was first washed with the mother liquor, and then with ice-cold water. The crystals were dried in air to give 565 mg. of 1-(3,5-di-O-acetyl-2-deoxy-β-D-erythropentofuranosyl)-2-thiothymine having a melting point at 155° to 160° C. About 545 mg. of the compound was recrystallized from a mixture of absolute ethanol and technical hexane, after decolorizing with with charcoal, to give 490 mg. of the analytically pure compound having a melting point at 162° to 164.5° C.

Optical Rotation: $[\alpha_D^{23°}$ —14°(C, 0.7192 in acetone)

Ultraviolet Absorption: $\lambda_{max.}^{95\% \ EtOH}$ 221; 277 mµ (ε15,350; 16,400)

Characteristic infrared absorption frequencies (cm.$^{-1}$)

NH/=CH, 3180, 3080; C=O, 1745, 1730; C=O/C=H/C=C, 1675, 1490; C—O/C—N/other, 1300, 1290, 1280, 1260, 1245, 1225, 1200, 1160, 1105, 1095, 1025, 960.

Analysis: Calc'd. for $C_{14}H_{18}N_2O_6S$: Found: C, 49.10; H, 5.30; N, 8.19; S, 9.37. Found: C, 49.20; H, 5.89; N, 8.19; S, 9.13.

EXAMPLE 5

Preparation of 1-(2-Deoxy-β-D-Erythropentofuranosyl)-2-Thiouracil and 3,5-Diacetate Thereof

Part A.
1(5-O-Tosyl-2-deoxy-β-D-erythropentofuranosyl)-uracil

While all moisture was excluded, a solution consisting of 1.18 g. (5.2 millimoles) 1-(2-deoxy-β-D-ribofuranosyl)-uracil and 6 ml. pyridine was chilled to 0° C. with stirring. At that temperature, 1.20 g. (0.63 millimole) p-toluenesulfonyl chloride dissolved in 6 ml. pyridine was added. The reaction vessel was securely stoppered and then set aside at a temperature of 3° to 5° C. for 3 days. At that time the excess p-toluenesulfonyl chloride was decomposed by the addition of crushed ice. After the ice had melted, the reaction mixture was poured into a separatory funnel containing 80 ml. water. The dilute aqueous solution was then extracted three times with 25 ml. portions of chloroform. The combined chloroform extracts were washed once with pure water, and then dried over anhydrous sodium sulfate. The chloroform was then removed by evaporation under reduced pressure, and the residue thus obtained was azeotroped three times with 95% aqueous ethanol. A white crystalline solid was obtained. Recrystallization from a mixture of acetone and technical hexane gave 1.0 g. of 1-(5-O-tosyl-2-deoxy-β-D-erythropentofuranosyl)uracil. Recrystallization of a 150 mg. sample of the compound again from the mixture of acetone and technical hexane gave an analytical sample of the compound having a melting point at 158° to 158.5° C.

Ultraviolet Absorption: $\lambda_{max.}^{95\% \ EtOH}$ 223; 261 mµ (ε15,350, 10,150).

Characteristic infrared absorption frequencies (cm.$^{-1}$) NH/OH/=CH, 3380, 3160, 3100, 3060; C=O, 1720, 1670; C=C, 1625, 1575; —SO$_2$—O/C—O/-C—N/other, 1365, 1270, 1190, 1180, 1175, 1090, 1065, 920; p-CH/other, 825, 815, 810.

Analysis: Calc'd. for $C_{16}H_{18}N_2O_7S$: C, 50.30; H, 4.75; N, 7.33; S, 8.39. Found: C, 50.63; H, 4.98; N, 7.08; S, 8.12.

Part B.
2,5'-Anhydro-1-(2-deoxy-β-D-erythropentofuranosyl)-uracil

In an environment of dry nitrogen, with moisture excluded, a reaction mixture consisting of 4.43 g. (11.6 millimoles) 1-(5-O-tosyl-2-deoxy-β-D-erythropentofuranosyl)-uracil (Part A, above), 150 ml. dimethylformamide, and 5.0 g. sodium bicarbonate was heated at a temperature of 145° C. for 50 mins. The reaction mixture was cooled to 25° C., filtered, and the filtrate saved. The dimethylformamide was removed by evaporation under reduced pressure, and the residue thus obtained was azeotroped two times with absolute ethanol under reduced pressure. The azeotroped residue was dissolved in hot 95% aqueous ethanol and 10 g. of silica gel was added to the solution. A dry mixture of reaction product and silica gel was obtained by removing the ethanol by evaporation under reduced pressure. The dry mixture was added to a 275 g. column of silica gel, previously wetted with "Solvent C" . The chromatograph was developed with "Solvent C". After removing the solvent from the eluate by evaporation, there was obtained 1.40 g. of crude 2,5'-anhydro-1-(2-deoxy-β-D-erythropentofuranosyl)uracil. Recrystallization of a 100 mg. sample from aqueous ethanol gave an analytical sample having a melting point at 182° to 184° C.

Ultraviolet Absorption: $\lambda_{max.}^{H_2O}$ 237; 255$_{sh.}$ mµ (ε 12,000; 7,800).

Characteristic infrared absorption frequencies (cm.$^{--1}$) OH, 3380, 3290; C=O/C=C/C=N, 1645, 1620$_{sh.}$, 1615, 1510; C—O/C—N/other, 1260, 1170, 1115, 1090, 1080; Arom. CH/other, 860, 835.

Analysis: Calc'd. for $C_9H_{10}N_2O_4$: C, 51.43; H, 4.80; N, 13.33. Found: C, 51.19; H, 4.45; N, 12.87.

Part C.
1-(2-Deoxy-β-D-erythropentofuranosyl)-2-)methyluracil

A reaction solution consisting of 260.9 mg. (1.24 millimoles) of 2,5'-anhydro-1-(2-deoxy-β-D-erythropentofuranosyl)uracil (Part B, above), 3 ml. dimethylformamide, 165 ml. absolute methanol, and 3.35 ml. triethylamine was securely sealed and set aside at 25°C. for 3 days. The solvents and volatile components were then removed from the reaction mixture by evaporation under reduced pressure. The residue thus obtained was azeotroped three times with absolute ethanol, the ethanol being removed under reduced pressure. The thus azeotroped residue was dissolved in 95% aqueous ethanol and 1.5 g. silica gel was added. After removing the aqueous ethanol from the solution by evaporation under reduced pressure, the dry silica gel mixture was added to a column of silica gel (35 g.) that had been wetted with "Solvent C". The column was developed with "Solvent C", and the solvent was removed from the fraction containing the desired compound by evaporation under reduced pressure, and the residue thus obtained was dissolved in methanol. After filtering to remove insoluble particles, the methanol was removed from the filtrate by evaporation under reduced pressure. There was thus obtained 1-(2-deoxy-$\beta$-D-erythropentofuranosyl)-2-O-methyluracil having a melting point at 134.5° to 136°C.

Ultraviolet Absorption: $\lambda_{max}.^{95\% EtOH}$ 228; 248 m$\mu$ ($\epsilon$11,300; 10,150), Characteristic infrared absorption frequencies (cm.$^{-1}$) NH/OH, 3400, 3000$_{brd.}$, 2720$_{sh.}$; C=O/C=N/C=C, 1640, 1610, 1500; C—O/C—N-/other, 1290, 1115, 1100, 1080, 1030, 1015; Other, 835.

Analysis: Calc'd. for $C_{10}H_{14}N_2O_5$: C, 49.58; H, 5.83; N, 11.57. Found: C, 49.31; H, 6.02; N, 11.42.

Part D.
1-(2-Deoxy-$\beta$-D-erythropentofuranosyl)-2-thiouracil

A solution consisting of 1-(2-deoxy-$\beta$-D-erythropentofuranosyl)-2-O-methyluracil (prepared as in Part C, above) and 50 ml. dimethylformamide containing 3.3 ml. of triethylamine was treated with hydrogen sulfide by slowly bubbling a stream of the gas into the solution for 17 hrs. Moisture was excluded and the temperature was 25°C. The treated solution was then purged with dry nitrogen gas in order to sweep out any excess hydrogen sulfide. The purged reaction solution was then transferred to a clean roundbottom flask, rinsing the reaction vessel with a small amount of dimethylformamide. The dimethylformamide was then removed by evaporation under reduced pressure, and the residue thus obtained was azeotroped with absolute ethanol under reduced pressure. The azeotroped residue was dissolved in hot absolute ethanol and 5.0 g. silica gel was added to the solution. After removing the ethanol by evaporation under reduced pressure, the dry silica gel mixture was added to a silica gel column (125 g.) prepared from a slurry of the silica gel in "Solvent A". The column was developed with "Solvent A" and 10 ml. fractions were collected. Fractions 41 through 59 were combined, and the "Solvent A" was removed by evaporation under reduced pressure. A white solid was obtained that was crystallized from a mixture of absolute ethanol and technical hexane to give 1-(2-deoxy-$\beta$-D-erythropentofuranosyl)-2-thiouracil having an idefinite melting point but apparently about 133° to 134° C.

Optical Rotation: $[\alpha]_D^{23°}$ +68° (C, 0.2524 in 0.1 N sodium hydroxide).

Ultraviolet Absorption: $\lambda_{max}.^{H_2O}$ 217; 274 m$\mu$ ($\epsilon$ 15,00; 12,950); $\lambda_{max}.^{0.1 N NaOH}$ 238; 269 m$\mu$ ($\epsilon$ 19,600; 12,650)

Characteristic infrared absorption frequencies (cm.$^{-1}$) NH/OH/=CH, 3390, 3180, 3060; C=O/C=C/"-C—N", 1675, 1655, 1485; "C=S"/C—O/C—N/other, 1280, 1195, 1165, 1140, 1115, 1090, 1040.

Part E.
1-(3,5-Di-O-acetyl-2-deoxy-$\beta$-D-erythropentofuranosyl)-2-thiouracil A suspension of 488 mg. (2.0 millimoles) of finely divided 1-(2-deoxy-$\beta$-D-erythropentofuranosyl)-2-thiouracil (Part D, above) in 4 ml. acetic anhydride containing 2 drops pyridine was heated at a bath temperature of 75° to 76°C. for 71 hrs. External moisture was excluded. The reaction mixture was then cooled and poured into a mixture of ice and water. When this ice and water mixture was stirred and the sides of the vessel scratched, crystallization initiated spontaneously. The crystallizing mixture was set aside for a few hours with an occasional rubbing and trituration. After refrigeration at 3° C., the crystals were collected on a filter. The filter cake was washed with the mother liquor, with ice-water, and then dried. There was thus obtained 430+ mg. of 1-(3,5-di-O-acetyl-2-deoxy-$\beta$-D-erythropentofuranosyl)-2-thiouracil. Recrystallization from a mixture of absolute ethanol and technical hexane after treatment with decolorizing charcoal gave 400 mg. of an analytical sample that had a melting point at 130° to 131°C.

Optical Rotation: $[\alpha]_D^{23°}$ 0° (C, 0.5320 in acetone).

Ultraviolet Absorption: $\lambda_{max}.^{95\% EtOH}$ 219; 274 m$\mu$ ($\epsilon$ 17,250; 14,500).

Characteristic infrared absorption frequencies (cm.$^{-1}$) NH, 3210, 3160; C=O, 1750, 1730, 1705; C=C/C=N, 1620, 1485; C=S/C—O/C—N/other, 1310, 1280, 1250, 1195, 1140, 1115, 1080, 1055, 1025; Arom. CH/other, 835.

Mass Spectroscopy: M$^+$ 328; B+1 128; deoxy-sugar$^+$ 201.

Analysis: Calc'd. for $C_{13}H_{16}N_2O_6S$: C, 47.55; H, 4.91; N, 8.53; S, 9.77. Found: C, 47.10; H, 4.86; N, 8.62; S, 9.58.

EXAMPLE 6

Preparation of
1-(2-Deoxy-$\beta$-D-Threopentofuranosyl)-2-Thiothymine

Part A.
1-(5-O-Tosyl-2-deoxy-$\beta$-D-threopentofuranosyl)thymine

While all moisture was excluded and the temperature was maintained at about 0° C., a solution consisting of 1.18 g. (6.2 millimoles) p-toluenesulfonyl chloride in 8 ml. pyridine was added with stirring to a substantially complete solution consisting of 1.20 g. (4.96 millimoles) of 1-(2-deoxy-$\beta$-D-threopentofuranosyl)thymine. This reaction mixture was securely sealed and refrigerated at a temperature of 3° to 5° C. overnight. In the morning, a small amount of crushed ice was added to the reaction mixture and refrigeration was continued at a temperature of 3° to 5° C. for an additional 2 hrs. The refrigerated reaction mixture was poured into 200 ml. ice-water, and the reaction flask was rinsed with 75 ml. water. The rinse was added to the ice-water mixture. This aqueous solution was transferred to a separatory funnel and extracted three times with 25 ml. chloroform. The chloroform extracts were combined, washed three times with saturated aqueous sodium bicarbonate, washed once with water, and dried over anhydrous sodium sulfate. After removing the chloroform by evaporation under reduced pressure, and azeotroping the thus obtained residue three times with absolute ethanol under reduced pressure, there was obtained a substantially pure compound as determined by thin layer chromatography using "Solvent A". Crystallization of the solid from a mixture of acetone and technical hexane gave 1.51 g. of 1-(5-O-tosyl-2-deoxy-β-D-threopentofuranosyl)thymine having a melting point at 163° to 164° C.

Ultraviolet Absorption: $\lambda_{max.}^{Ab.\ EtOH}$ 224; 266, 272$_{sh}$. m$\mu$ ($\epsilon$ 16,700, 9,750; 9,000).

Characteristic infrared absorption frequencies (cm.$^{-1}$) NH/OH/=CH, 3420, 3180, 3050; C=O/C=λ C/other, 1715, 1695, 1970$_s$; C=C, 1600; —SO$_2$—O/-C—O/other, 1370, 1355, 1275, 1195, 1180; Unidentified, 985, 965$_s$; Arom. CH/other, 860, 775.

Analysis: Calc'd. for $C_{17}H_{20}N_2O_2O_7S$: C, 51.56; H, 5.09; N, 7.07; S, 8.10. Found: C, 52.01; H, 5.46; N, 7.02; S, 8.36.

Part B.
2,5'-Anhydro-1-(2-deoxy-β-D-threopentofuranosyl)-thymine

In an environment of gaseous nitrogen, a mixture consisting of 800 mg. 1-(5-O-tosyl-2-deoxy-β-D-threopentofuranosyl)thymine (Part A, above), 30 ml. dimethylformamide, and 2 g. sodium bicarbonate was heated, with stirring, at a bath temperature of 130° to 150° C. for 75 mins. The reaction mixture was cooled and filtered. The filter was washed with dimethylformamide and the filtrate and washings were combined. After removing the dimethylformamide by evaporation under reduced pressure, the residue thus obtained was dissolved in aqueous ethanol and 2 g. of silica gel was added to the solution. The ethanol was removed by evaporation under reduced pressure to give a dry silica gel mixture. This mixture was added to a column of silica gel that had been wetted with "Solvent C". After developing the chromatograph with "Solvent C" and collecting the eluate, the "Solvent C" was removed from the eluate by evaporation under reduced pressure. The residue thus obtained was azeotroped with ethanol, under reduced pressure. This azeotroped residue was crystallized from absolute ethanol and dried under reduced pressure at 40° C. to give 179 mg. of 2,5'-anhydro-1-(2-deoxy-β-D-threopentofuranosyl)thymine having a melting point at 228° to 230° C.

Ultraviolet Absorption: $\lambda_{max.}^{Ab.\ EtOH}$ 240$_{sh}$; 246 m$\mu$ ($\epsilon$ 8,150; 8,200).

Characteristic infrared absorption frequencies (cm.$^{-1}$) OH, 3530, 3380, 3280; C=O/C=N/C=C, 1665, 1630, 1535, 1485; C—O/C—N/other, 1275, 1140, 1080, 1050, 975, 900, 880, 810, 790.

Analysis: Calc'd. for $C_{10}H_{12}N_2O_4$: C, 53.57; H, 5.39; N, 12.50. Found: C, 53.49; H, 5.81; N, 11.80.

Part C.
1-(2-Deoxy-β-D-threopentofuranosyl)-2-O-methyl-thymine

After adding 18 mg. (0.323 millimole) sodium methoxide to a lukewarm solution of 224.0 mg. (1.0 millimole) 2,5'-anhydro-1-(2-deoxy-β-D-threopentofuranosyl)thymine (Part B, above) in a solvent mixture consisting of 2 ml. dimethylformamide and 20 ml. absolute methanol, the reaction vessel was securely sealed and set aside at a temperature of 25° C. After several days a further 150 mg. (27.8 millimoles) of sodium methoxide was added. After another 6 days, the reaction mixture was neutralized by dropwise additions of glacial acetic acid. The solvents dimethylformamide and methanol were removed by evaporation under reduced pressure, and the residue thus obtained was azeotroped two times with absolute ethanol under reduced pressure. The azeotroped residue was dissolved in hot 95% aqueous ethanol and 2.5 g. of silica gel was added. The aqueous ethanol was removed by evaporation under reduced pressure, and the dry silica gel mixture was added to a column of silica gel (25 g.) previously wetted with 4 ml. of "Solvent C". The column was developed with "Solvent C". Removal of the "Solvent C" from the eluate under reduced pressure gave 116.7 mg. of 1-(2-deoxy-β-D-threopentofuranosyl)-2-O-methyl-thymine having a melting point at 159° to 161° C.

Ultraviolet Absorption: $\lambda_{max.}^{MeOH}$ 235$_{sh}$; 254 ($\epsilon$ 8,400, 10,250).

Characteristic infrared absorption frequencies (cm.$^{-1}$) OH, 3400, 3100, 2760$_{sh}$, 2660$_{sh}$; C=O/C=N/C=C, 1660, 1615, 1525, 1485; C—O/-C—N/other, 1295, 1255, 1225, 1190, 1140, 1110, 1075, 1060, 1010, 990; Other, 870.

Part D.
1-(2-Deoxy-β-D-threopentofuranosyl)-2-thiothymine

A solution consisting of 106 mg. (0.415 millimole) of 1-(2-deoxy-β-D-threopentofuranosyl)-2-O-methylthymine (Part C, above), 5 ml. dimethylformamide, and 12 drops of triethylamine was treated with a slowly bubbled stream of hydrogen sulfide gas for 22 ½ hrs. Afterwards, the dimethylformamide and volatile components of the reaction mixture were removed by evaporation under reduced pressure. The residue thus obtained was azeotroped two times with absolute ethanol under reduced pressure. After determining by thin layer chromatography that a large proportion of starting material was present, the azeotroped residue was dissolved in warm dimethylformamide, 7 drops of triethylamine were added and the treatment with hydrogen sulfide gas was continued for 2 days. The treated reaction mixture was evaporated under reduced pressure, and the residue thus obtained was azeotroped with absolute ethanol under reduced pressure. The azeotroped residue was dissolved in 95% aqueous ethanol and 1 g. of silica gel was added. After removing the aqueous ethanol by evaporation under reduced pressure the silica gel and reaction product mixture was added to a chromatographic column of silica gel (25 g.) that had been wetted with "Solvent C". The column was developed with "Solvent C" and 3 ml. fractions were collected. Fractions 14 through 17 were combined and the solvent was removed by evaporation under reduced pressure. The residue thus obtained was crystallized from a mixture of acetone and ethylacetate to give 1-(2-deoxy-β-D-threopentofuranosyl)-2-thiothymine having a melting point at 168.5° to 171° C. with resolidification at 175° C.

Ultraviolet Absorption: $\lambda_{max.}^{95\%\ EtOH}$ 221; 274; 288$_{sl.sh}$. m$\mu$ ($\epsilon$ 14,050; 14,900; 13,150)

Characteristic infrared absorption frequencies (cm.$^{-1}$) NH/OH, 3410, 3250; C=O/C=C/C=N, 1690$_s$, 1650, 1510, 1485; C—N/C=S/C—O/other, 1300, 1285, 1265, 1130, 1105, 1060, 1030.

EXAMPLE 7

Preparation of 1-(3-Deoxy-β-D-Threopentofuranosyl)-2-Thiouracil

Part A.
1-(5-O-Tosyl-3-deoxy-β-D-threopentofuranosyl)-uracil

With moisture excluded, a solution consisting of 228 mg. (1.0 millimoles) of 1-(3-deoxy-β-D-threopentofuranosyl)-uracil [Prepared according to the method described by Horwitz et al., J. Org. Chem. 31, pp. 205—211 (1966)] and 2.5 ml. pyridine was chilled to 0° C. and a solution consisting of 236 mg. (1.24 millimoles) p-toluenesulfonyl chloride and 2.5 ml. pyridine was added dropwise while the temperature of the reaction mixture was maintained at 0° C. The reaction vessel was securely sealed and set aside at 3° to 5° C. for about 16 hrs. Afterwards, a small portion of crushed ice was added to the reaction mixture and refrigeration was continued for about 1 to 2 hrs. This mixture was further diluted with 50 ml. of ice-cold water and the dilute aqueous solution was extracted three times with 30 ml. portions of chloroform. The chloroform extracts were combined and dried over anhydrous sodium sulfate. After removing the chloroform by evaporation under reduced pressure, the residue thus obtained was dissolved in hot absolute ethanol. Some decolorizing charcoal was added to the ethanol solution, the charcoal was removed by filtration, and the filter was washed with hot absolute ethnol. The ethanol was removed from the combined filtrate and washings under reduced pressure, and the residue thus obtained was azeotroped with absolute ethanol under reduced pressure. There was thus obtained 182.8 mg. of 1-(5-O-tosyl-3-deoxy-β-D-threopentofuranosyl)uracil as an amorphous solid.

Ultraviolet Absorption: $\lambda_{max}^{95\%\ EtOH}$ 233; 262; $272_{sl.sh.}$ ($\epsilon$ 15,500; 10,300; 7,900)

Characteristic infrared absorption frequencies (cm.$^{-1}$) NH/OH, $3340_{brd.}$; C=O/C=C/C=N, $1705_{sh.}$, 1685, $1625_{sh.}$, $1595_w$.; —SO$_2$-O/C—O/C—N/other, 1360, 1280, 1190, 1175, 1110, 1095, 1085, 955.

Analysis: Calc'd. for C$_{16}$H$_{18}$N$_2$O$_7$S: C, 50.30; H, 4.74; N, 7.38; S, 8.38. Found: C, 50,89; H, 5.10; N, 6.66; S, 8.07.

Part B.
2,2'-Anhydro-1-(3-deoxy-β-D-threopentofuranosyl)-uracil

A reaction mixture consisting of 1.54 g. (4.03 millimoles) of 1-(5-O-tosyl-3-deoxy-β-D-threopentofuranosyl)-uracil (prepared as in Part A, above), 1.5 g. sodium bicarbonate, and 50 ml. dimethylformamide was heated, with stirring and in the presence of nitrogen gas at a bath temperature of 150° C. for 65 mins. After cooling the reaction mixture to about 25° C., it was filtered, and the filter was washed with dimethylformamide. The dimethyl-formamide was removed substantially completely by evaporation under reduced pressure, and the residue thus obtained was azeotroped three times with absolute ethanol under reduced pressure. The azeotroped dry solid thus obtained was dissolved in 95% aqueous ethanol and 5 g. of silica gel was added. This slurry was taken to dryness by evaporating the aqueous ethanol under reduced pressure. The dry silica gel mixture was added to a chromatographic column of silica gel (100 g.) that had been wetted with "Solvent C". The column was developed with "Solvent C", and the eluate was collected. After removing the solvent by evaporation under reduced pressure, crystallizing the residue thus obtained from a mixture of absolute ethanol and technical hexane, and drying the crystals at 40° C. under reduced pressure, there was obtained 160.3 mg. of 2,2'-anhydro-1-(3-deoxy-β-D-threopentofuranosyl)uracil having a melting point at 214° to 216° C.

Ultraviolet Absorption: $\lambda_{max}^{water}$ 223; 235; $260_{sh.}$; $269_{sh.}$ m$\mu$ ($\epsilon$ 8,350; 8,100; 6,250; 2,400)

Characteristic infrared absorption frequencies (cm.$^{-1}$) OH, 3320; C=O/C=N/C=C, 1475; C—O/-C—N/other, 1240, 1095, 1040; =CH/other, 830.

Analysis: Calc'd. for C$_9$H$_{10}$N$_2$O$_4$: C, 51.42; H, 4.80; N, 13.33. Found: C, 51.49; H, 5.04; N, 13.65.

Part C.
1-(3-Deoxy-β-D-threopentofuranosyl)-2-thiouracil

A solution consisting of 42 mg. (0.2 millimole) of 2,2'-anhydro-1-(3-deoxy-β-D-threopentofuranosyl)uracil (Part B, above), 2 ml. dimethylformamide, and 0.1 ml. triethylamine was treated with hydrogen sulfide by slowly bubbling a stream of the gas through the solution for 114 hrs. Small, additional amounts of triethylamine were added from time to time. Afterwards, excess hydrogen sulfide was removed by purging the reaction solution with nitrogen gas, and the dimethylformamide was removed by evaporation under reduced pressure. The residue thus obtained was azeotroped two times with absolute ethanol under reduced pressure. The azeotroped residue was dissolved in 5 ml. 95% aqueous ethanol and 1 g. of silica gel was added. This slurry was taken to dryness by evaporating the aqueous ethanol under reduced pressure. The dry silica gel mixture was added to a chromatographic column of silica gel (18 g.) that had been wetted with "Solvent A". The column was developed with "Solvent A" and the fraction containing the desired compound was taken to dryness by removing the solvent by evaporation under reduced pressure, and the residue thus obtained was crystallized from a mixture of absolute ethanol and technical hexane. There was thus obtained 26.6 mg. of 1-(3-deoxy-β-D-threopentofuranosyl)-2-thiouracil having a melting point at 161° to 163° C.

Ultraviolet Absorption: $\lambda_{max}^{95\%\ EtOH}$ 220; 275; $283_{sl.sh.}$ m$\mu$ ($\epsilon$ 16,750; 14,200; 13,800)

Characteristic infrared absorption frequencies (cm.$^{-1}$) OH/NH, 3390, 3200; C=O, 1670; C=N/C=C, 1495; C=S/C—O/other, 1285, 1150, 1115, 1100; other, 820.

Analysis: Calc'd. for C$_9$H$_{12}$N$_2$O$_4$S: C, 44.25; H, 4.95; N, 11.47; S, 13.13. Found: C, 44.30; H, 4.79; N, 12.28; S, 12.67.

EXAMPLE 8

Following the procedure of Example 4, Part C, but substituting 1-β-D-ribofuranosyl-2-thio-6-azauracil,
1-β-D-ribofuranosyl-2-thiouracil,
1-β-D-ribofuranosyl-2-thiothymine,
1-(2-deoxy-β-D-threopentofuranosyl)-2-thiothymine, and
1-(3-deoxy-β-D-threopentofuranosyl)-2-thiouracil for 1-(2-deoxy-β-D-erythropentofuranosyl)-2-thiothymine, there is prepared
1-(2,3,5-tri-O-acetyl-β-D-ribofuranosyl)-2-thio-6-azauracil, Optical Rotation: $[\alpha]_D^{23°}$ −44° (C, 1.0668 in CHCl₃).

Ultraviolet Absorption: $\lambda_{max}^{ethanol}$ 217; 271; 315$_{sl.sh.}$ mµ (ε 14,100; 17,850; 2,050)

Characteristic infrared absorption frequencies (cm.⁻¹) OH, ~3400$_{brd.}$; NH/OH/=CH, 3210, 3140, 3070; C=O, 1745, 1720; C—O/other, 1330, 1235, 1185, 1090, 1050, 990, 935, 900.

Analysis: Calc'd for C₁₄H₁₇N₃O₈S: C, 43.45; H, 4.42; N, 10.85; S, 8.28. Found: C, 42.98; H, 4.48; N, 10.76; S, 8.57.

1-(2,3,5-tri-O-acetyl-β-D-ribofuranosyl)-2-thiouracil,
1-(2,3,5-tri-O-acetyl-β-D-ribofuranosyl)-2-thiothymine, 1-(3,5,-di-O-acetyl-2-deoxy-β-D-threopentofuranosyl)-2-thiothymine, and
1-(2,5-di-O-acetyl-3deoxy-β-D-threopentofuranosyl)-2-thiouracil, respectively.

EXAMPLE 9

Following the procedure of Example 4, Part C, but separately substituting propionic anhydride, butyric anhydride, benzoic anhydride and anisoic anhydride for acetic anhydride, there is prepared, 1-(3,5-di-O-propionyl-2-deoxy-β-D-erythropentofuranosyl)-2-thiothymine,
1-(3,5-di-O-butyryl-2-deoxy-β-D-erythropentofuranosyl)-2-thiothymine,
1-(3,5-di-O-benzoyl-2-deoxy-β-D-erythropentofuranosyl)-2-thiothymine, and
1-(3,5-di-O-anisoyl-2-deoxy-β-D-erythropentofuranosyl)-2-thiothymine, respectively.

EXAMPLE 10
Part A.

Following the procedure of Example 3, Part A, but substituting 1-(β-D-ribofuranosyl)-5-ethyluracil,
1-(β-D-ribofuranosyl)-5-butyluracil,
1-(β-D-ribofuranosyl)-5-hydroxymethyluracil,
1-(β-D-ribofuranosyl)-5-methoxymethyluracil,
1-(β-D-ribofuranosyl)-5-acetoxymethyluracil, and
1-(β-D-ribofuranosyl)-5-ethoxymethyluracil for 1-β-D-ribofuranosylthymine, there is prepared,
1-(2,3-O-isopropylidene-β-D-ribofuranosyl)-5-ethyluracil,
1-(2,3-O-isopropylidene-β-D-ribofuranosyl)-5-butyluracil,
1-(2,3-O-isopropylidene-β-D-ribofuranosyl)-5-hydroxy-methyluracil,
1-(2,3-O-isopropylidene-β-D-ribofuranosyl)-5-methoxy-methyluracil,
1-(2,3-O-isopropylidene-β-D-ribofuranosyl)-5-acetoxy-methyluracil, and
1-(2,3-O-isopropylidene-β-D-ribofuranosyl)-5-ethoxy-methyluracil, respectively.

Part B.

Following the procedure of Example 3, Part B, but separately substituting 1-(2,3-O-isopropylidene-β-D-ribofuranosyl)-5-ethyluracil,
1-(2,3-O-isopropylidene-β-D-ribofuranosyl)-5butyluracil,
1-(2,3-O-isopropylidene-β-D-ribofuranosyl)-5-hydroxy-methyluracil,
1-(2,3-O-isopropylidene-β-D-ribofuranosyl)-5-methoxy-methyluracil,
1-(2,3-O-isopropylidene-β-D-ribofuranosyl)-5-acetoxy-methyluracil, and
1-(2,3-O-isopropylidene-β-D-ribofuranosyl)-5-ethoxy-methyluracil for 1-(2,3-O-isopropylidene-β-D-ribofuranosyl)-thymine, there is prepared
1-(5-O-tosyl-2,3-O-isopropylidene-β-D-ribofuranosyl)-5-ethyluracil,
1-(5-O-tosyl-2,3-O-isopropylidene-β-D-ribofuranosyl)-5-butyluracil,
1-(5-O-tosyl-2,3-O-isopropylidene-β-D-ribofuranosyl)- 5-hydroxymethyluracil,
1-(5-O-tosyl-2,3-O-isopropylidene-β-D-ribofuranosyl)-5-methoxymethyluracil,
1-(5-O-tosyl-2,3-O-isopropylidene-β-D-ribofuranosyl)-5-acetoxymethyluracil, and
1-(5-O-tosyl-2,3-O-isopropylidene-β-D-ribofuranosyl)-5-ethoxymethyluracil, respectively.

Part C.

Following the procedure of Example 3, Part C, but separately substituting 1-(5-O-tosyl-2,3-O-isopropylidene-β-D-ribofuranosyl)-5-ethyluracil,
1-(5-O-tosyl-2,3-O-isopropylidene-β-D-ribofuranosyl)-5-butyluracil,
1-(5-O-tosyl-2,3-O-isopropylidene-β-D-ribofuranosyl)-5-hydroxymethyluracil,
1-(5-O-tosyl-2,3-O-isopropylidene-β-D-ribofuranosyl)-5-methoxymethyluracil,
1-(5-O-tosyl-2,3-O-isopropylidene-β-D-ribofuranosyl)-5-acetoxymethyluracil, and
1-(5-O-tosyl-2,3-O-isopropylidene-β-D-ribofuranosyl)-5-ethoxymethyluracil, for 1-(5-O-tosyl-2,3-O-isopropylidene-β-D-ribofuranosyl)thymine, there is prepared:
2,5'-anhydro-1-(2,3-O-isopropylidene-β-D-ribofuranosyl)-5-ethyluracil,
2,5'-anhydro-1-(2,3-O-isopropylidene-β-D-ribofuranosyl)-5-butyluracil,
2,5'-anhydro-1-(2,3-O-isopropylidene-β-D-ribofuranosyl)-5-hydroxymethyluracil,
2,5'-anhydro-1-(2,3-O-isopropylidene-β-D-ribofuranosyl)-5-methoxymethyluracil,
2,5'-anhydro-1-(2,3-O-isopropylidene-β-D-ribofuranosyl)-5-acetoxymethyluracil, and
2,5'-anhydro-1-(2,3-O-isopropylidene-β-D-ribofuranosyl)-5-ethoxymethyluracil, respectively.

Part D.

Following the procedure of Example 3, Part D, but separately substituting 2,5'-anhydro-1-(2,3-O-isopropylidene-β-D-ribofuranosyl)-5-ethyluracil,
2,5'-anhydro-1-(2,3-O-isopropylidene-β-D-ribofuranosyl)-5-butyluracil,
2,5'-anhydro-1-(2,3-O-isopropylidene-β-D-ribofuranosyl)-5-hydroxymethyluracil,
2,5'-anhydro-1-(2,3-O-isopropylidene-β-D-ribofuranosyl)-5-methoxymethyluracil,
2,5'-anhydro-1-(2,3-O-isopropylidene-β-D-ribofuranosyl)-5-acetoxymethyluracil, and
2,5'-anhydro-1-(2,3-O-isopropylidene-β-D-ribofuranosyl)-5-ethoxymethyluracil for 2,5'-anhydro-1-(2,3-O-isopropylidene-β-D-ribofuranosyl)thymine, there is prepared,
1-(2,3-O-isopropylidene-β-D-ribofuranosyl)-5-ethyl-2-O-methyluracil,
1-(2,3-O-isopropylidene-β-D-ribofuranosyl)-5-butyl-2-O-methyluracil,
1-(2,3-O-isopropylidene-β-D-ribofuranosyl)-5-hydroxy-methyl-2-O-methyluracil, 1-(2,3-O-isopropylidene-β-D-ribofuranosyl)-5-methoxy-methyl-2-O-methyluracil, 1-(2,3-O-isopropylidene-β-D-ribofuranosyl)-5-acetoxy-methyl-2-O-methyluracil, and 1-(2,3-O-isopropylidene-β-D-ribofuranosyl)-5-ethoxy-methyl-2-O-methyluracil, respectively.

Part E.

Following the procedure of Example 3, Part E, but separately substituting 1-(2,3-O-isopropylidene-β-D-ribofuranosyl)-5-ethyl-2-O-methyluracil, 1-(2,3-O-isopropylidene-β-D-ribofuranosyl)-5-butyl-2-O-methyluracil, 1-(2,3-O-isopropylidene-β-D-ribofuranosyl)-5-hydroxy-methyl-2-O-methyluracil, 1-(2,3-O-isopropylidene-β-D-ribofuranosyl)-5-methoxy-methyl-2-O-methyluracil, 1-(2,3-O-isopropylidene-β-D-ribofuranosyl)-5-acetoxy-methyl-2-O-methyluracil, and 1-(2,3-O-isopropylidene-β-D-ribofuranosyl)-5-ethoxy-methyl-2-O-methyluracil, for 1-(2,3-O-isopropylidene-β-D-ribofuranosyl)-2-0-methylthymine there is prepared, 1-(2,3-O-isopropylidene-β-D-ribofuranosyl)-5-ethyl-2-thiouracil, 1-(2,3-O-isopropylidene-β-D-ribofuranosyl)-5-butyl-2-thiouracil, 1-(2,3-O-isopropylidene-β-D-ribofuranosyl)-5-hydroxy-methyl-2-thiouracil, 1-(2,3-O-isopropylidene-β-D-ribofuranosyl)-5-methoxy-methyl-2-thiouracil, 1-(2,3-O-isopropylidene-β-D-ribofuranosyl)-5-acetoxy-methyl-2-thiouracil, and 1-(2,3-O-isopropylidene-β-D-ribofuranosyl)-5-ethoxy-methyl-2thiouracil, respectively.

Part F.

Following the procedure of Example 3, Part F, but separately substituting 1-(2,3-O-isopropylidene-β-D-ribofuranosyl)-5-ethyl-2-thiouracil, 1-(2,3-O-isopropylidene-β-D-ribofuranosyl)-5-butyl-2-thiouracil, 1-(2,3-O-isopropylidene-β-D-ribofuranosyl)-5-hydroxy-methyl-2-thiouracil, 1-(2,3-O-isopropylidene-β-D-ribofuranosyl)-5-methoxy-methyl-2-thiouracil, 1-(2,3-O-isopropylidene-β-D-ribofuranosyl)-5-acetoxy-methyl-2-thiouracil, and 1-(2,3-O-isopropylidene-β-D-ribofuranosyl)-5-ethoxy-methyl-2-thiouracil, for 1-(2,3-O-isopropylidene-β-D-ribofuranosyl)-2-thiothymine, there is prepared:

1-β-D-ribofuranosyl-5-ethyl-2-thiouracil,

1β-D-ribofuranosyl-5-butyl-2-thiouracil,

1-β-D-ribofuranosyl-5-hydroxymethyl-2-thiouracil,

1-β-D-ribofuranosyl-5-methoxymethyl-2-thiouracil,

1-β-D-ribofuranosyl-5-acetoxymethyl-2-thiouracil, and

1-β-D-ribofuranosyl-5-ethoxymethyl-2-thiouracil, respectively.

EXAMPLE 11

Alternative Preparation of 1-(2-Deoxy-β-D-Erythropentofuranosyl)-2-Thiothymine

Part A.
1-(5-O-Tosyl-2-deoxy-β-D-erythropentofuranosyl)-thymine

A solution consisting of 2.36 g. (12.0 millimoles) p-toluenesulfonyl chloride in 12 ml. pyridine was slowly added dropwise, with stirring, to a solution consisting of 2.42 g. (10.0 millimoles) 1-(2-deoxy-β-D-erythropentofuranosyl)thymine and 12 ml. pyridine chilled to 0° C. Moisture was excluded. This reaction mixture was stoppered securely and set aside in a refrigerator at a temperature of 3° to 5° C. for 17 hrs.

After adding a small amount of crushed ice, refrigeration was continued for another hour. The chilled reaction mixture was then poured into about 75 ml. of crushed ice and water. The dilute aqueous mixture was allowed to warm to 25° C. and it was extracted three times with 50 ml. portions of chloroform. The chloroform extracts were combined and washed three times with saturated aqueous sodium bicarbonate, and once with water. The washed chloroform solution was then dried over anhydrous sodium sulfate. After removing the chloroform by evaporation under reduced pressure, azeotroping the residue with absolute ethanol under reduced pressure, and crystallizing the white solid thus obtained from 95% aqueous ethanol using decolorizing charcoal, and drying under reduced pressure at 40° C., there was obtained 2.22 g. of 1-(5-O-tosyl-2-deoxy-β-D-erythropentofuranosyl)thymine having a melting point at 170° to 171.5° C.

Ultraviolet Absorption: $\lambda_{max.}^{Ab. EtOH}$ 223; 265; 272$_{sh.}$ ($\epsilon$17,000; 9,800; 8,850)

Characteristic infrared absorption frequencies (cm.$^{-1}$) OH/NH/=CH, 3370, 3160; 3100, 3040; C=O/C=C, 1720, 1655, 1595; —SO$_2$O/C—O/other, 1360, 1275, 1190, 1175, 1095, 1075, 925, 920; p-CH/other, 830, 820.

Analysis: Calc'd. for $C_{17}H_{20}N_2O_7S$: C, 51.6; H, 5.09; N, 7.07; S, 8.10. Found: C, 51.83; H, 5.05; N, 6.69; S, 8.92.

Part B.
2,5'-Anhydro-1-(2-deoxy-β-D-erythropentofuranosyl)thymine

A reaction mixture consisting of 1.98 g. (5.0 millimoles) of 1-(5-O-tosyl-2-deoxy-β-D-erythropentofuranosyl)-thymine (Part A, above), 60 ml. dimethylformamide and 5 g. sodium bicarbonate was heated and stirred in a nitrogen environment for 2 hrs. at a bath temperature of 122° to 154° C. The reaction mixture was then cooled to about 25° C., filtered, and the filter washed with dimethylformamide. After combining the filtrate and washings, the dimethyl-formamide was removed by evaporation under reduced pressure, and the residue thus obtained was azeotroped under reduced pressure with 95% aqueous ethanol. The azeotroped residue was dissolved again in 95% aqueous ethanol and 5 g. silica gel was added to the solution. The aqueous ethanol was removed from the slurry by evaporation under reduced pressure and the dry silica gel:compound mixture was added to a chromatographic column of silica gel (150 g.). The column was developed with "Solvent C" and 750 ml. of eluate was collected. After removing the "Solvent C" by evaporation under reduced pressure, there was obtained 660 mg. of 2,5′-anhydro-1-(2-deoxy-β-D-erythropentofuranosyl)thymine having a melting point at 193° to 197° C.

Ultraviolet Absorption: $\lambda_{max.}^{95\% \ EtOH}$ 246 mμ

Part C.
1-(2-Deoxy-β-D-erythropentofuranosyl)-2-O-methyl thymine

A reaction solution consisting of 7.96 g. (31.2 millimoles) of 2,5′-anhydro-1-(2-deoxy-β-D-erythropentofuranosyl)-thymine (Part B, above), 76 ml. dimethylformamide, 760 ml. absolute methanol, and 765 mg. (14.15 millimoles) sodium methoxide was set aside in a securely stoppered flask for 19 hrs. The reaction solution was then neutralized by slow, dropwise addition of glacial acetic acid. A small amount of flocculent precipitate was removed by filtration, and the solvents were removed from the filtrate by evaporation under reduced pressure. The residue thus obtained was azeotroped under reduced pressure with absolute ethanol. There was thus obtained 8.56 g. of 1-(2-deoxy-β-D-erythropentofuranosyl)-2-O-methylthymine contaminated with small amounts of sodium acetate, but suitable for the reaction with hydrogen sulfide.

EXAMPLE 12

Part A.

Following the procedure of Example 11, Part A, but separately substituting 1-(2-deoxy-β-D-erythropentofuranosyl)-6-azauracil, 1-(2-deoxy-β-D-erythropentofuranosyl)-5-methyl-6-azauracil [both prepared according to the method described by Pliml, Prystaš, and Šorm, Collection Czechoslov. Chem. Commun. 28, pp. 2588–2596 (1963)], 1-β-D-arabino-furanosyl-6-azauracil, and 1-β-D-arabinofuranosyl-5-methyl-6-azauracil for 1-(2-deoxy-β-D-erythropentofuranosyl)thymine there is prepared
  1-(5-O-tosyl-2-deoxy-β-D-erythropentofuranosyl)-6-azauracil,
  1-(5-O-tosyl-2-deoxy-β-D-erythropentofuranosyl)-5-methyl-6-azauracil,
  1-(5-O-tosyl-β-D-arabinofuranosyl)-6-azauracil, and
  1-(5-O-tosyl-β-D-arabinofuranosyl)-5-methyl-6-azauracil, respectively.

Part B.

Following the procedure of Example 11, Part B, but separately substituting
  1-(5-O-tosyl-2-deoxy-β-D-erythropentofuranosyl)-6-azauracil,
  1-(5-O-tosyl-2-deoxy-β-D-erythropentofuranosyl)-5-methyl-6-azauracil,
  1-(5-O-tosyl-β-D-arabinofuranosyl)-6-azauracil, and
  1-(5-O-tosyl-β-D-arabinofuranosyl)-5-methyl-6-azauracil for 1-(5-O-tosyl-β-D-erythropentofuranosyl)thymine, there is prepared:
  2,5′-anhydro-1-(2-deoxy-β-D-erythropentofuranosyl)-6-azauracil,
  2,5′-anhydro-1-(2-deoxy-β-D-erythropentofuranosyl)-5-methyl-6-azauracil,
  2,5′-anhydro-1-β-D-arabinofuranosyl-6-azauracil, and
  2,5′-anhydro-1β-D-arabinofuranosyl-5-methyl-6-azauracil, respectively.

Part C.

Following the procedure of Example 11, Part C, but separately substituting
  2,5′-anhydro-1-(2-deoxy-β-D-erythropentofuranosyl)-6-azauracil,
  2,5′-anhydro-1-(2-deoxy-β-D-erythropentofuranosyl)-5-methyl-6-azauracil,
  2,5′-anhydro-1-β-D-arabinofuranosyl-6-azauracil, and
  2,5′-anhydro-1-β-D-arabinofuranosyl-5-methyl-6-azauracil, for 2,5′-anhydro-1-(2-deoxy-β-D-erythropentofuranosyl)thymine, there is prepared:
  1-(2-deoxy-β-D-erythropentofuranosyl)-2-O-methyl-6-azauracil,
  1-(2-deoxy-β-D-erythropentofuranosyl)-2-O-methyl-5-methyl-6-azauracil,
  1-β-D-arabinofuranosyl-2-O-methyl-6azauracil, and
  1-β-D-arabinofuranosyl-2-O-methyl-5-methyl-6-azauracil, respectively.

Part D

Following the procedure of Example 4, Part B, but separately substituting
  1-(2-deoxy-β-D-erythropentofuranosyl)-2-O-methyl-6-azauracil,
  1-(2-deoxy-β-D-erythropentofuranosyl)-2-O-methyl-5-methyl-6-azauracil,
  1-β-D-arabinofuranosyl-2-O-methyl-6-azauracil, and
  1-β-D-arabinofuranosyl-2-O-methyl-5-methyl-6-azauracil for 1-(2-deoxy-β-D-erythropentofuranosyl)-2-O-methylthymine, there is prepared:
  1-(2-deoxy-β-D-erythropentofuranosyl)-2-thio-6-azauracil,
  1-(2-deoxy-β-D-erythropentofuranosyl)-2-thio-5-methyl-6-azauracil,
  1-β-D-arabinofuranosyl-2-thio-6-azauracil, and
  1β-D-arabinofuranosyl-5-methyl-2-thio-6-azauracil, respectively.

Part E

Following the procedure of Example 4, Part C, but separately substituting
  1-(2-deoxy-β-D-erythropentofuranosyl)-2-thio-6-azauracil,
  1-(2-deoxy-β-D-erythropentofuranosyl)-2-thio-5-methyl-6-azauracil,
  1-β-D-arabinofuranosyl-2-thio-6-azauracil, and
  1-β-D-arabinofuranosyl-5-methyl-2-thio-6-azauracil for 1-(2-deoxy-β-D-erythropentofuranosyl)-2-thiothymine, there is prepared:
  1-(3,5-di-O-acetyl-2-deoxy-β-D-erythropentofuranosyl)-2-thio-6-azauracil,
  1-(3,5-O-acetyl-2-deoxy-β-D-erythropentofuranosyl)-5-methyl-2-thio-6-azauracil,
  1-(2,3,5-tri-O-acetyl-β-D-arabinofuranosyl)-2-thio-6-azauracil, and
  1-(2,3,5-tri-O-acetyl-β-D-arabinofuranosyl)-5-methyl-2-thio-6-azauracil, respectively.

We claim:

1. The process consisting of reacting a (2,5′-anhydro-1-β-D-pentofuranosyl)uracil or (2,5′-anhydro-1-β-D-pentafuranosyl)-6-azauracil nucleoside, having the following structural formula:

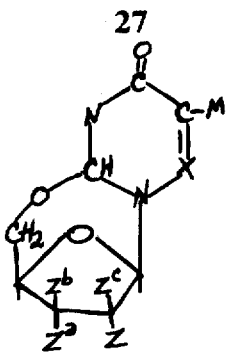

wherein X is CH or N, M is a member selected from the group consisting of hydrogen, lower alkyl of from 1 to 4 carbon atoms, inclusive, hydroxy-lower alkyl of from 1 to 3 carbon atoms, inclusive, loweralkoxymethyl wherein the alkoxy is from 1 to 4 carbon atoms, inclusive, and the acetic, propionic or butyric esters of the said hydroxyloweralkyl, and Z, $Z^a$, $Z^b$, and $Z^c$ are selected from the group consisting of hydrogen, hydroxy, and alkoxy of from 1 to 3 carbon atoms, inclusive with methanol in the presence of an alkali metal alkoxide to produce the corresponding 1-β-D-pentofuranosyl-2-O-methyluracil or 2-O-methyl-6-azauracil, respectively and treating the latter intermediates with hydrogen sulfide to obtain the corresponding 1-β-D-pentofuranosyl-2-thiouracil or -2-thio-6-azauracil respectively.

2. The process according to claim 1 wherein the pentofuranosyl group is 2- or 3-deoxy.

3. The process according to claim 2 wherein sodium methoxide is used.

4. The process according to claim 1 wherein sodium methoxide is used.

* * * * *